US005092882A

United States Patent [19]

Lynn et al.

[11] Patent Number: 5,092,882
[45] Date of Patent: Mar. 3, 1992

[54] MULTIPLE COMPARTMENT BREAST PROSTHESIS

[76] Inventors: Lawrence A. Lynn, 1275 Olentangy River Rd., Ste. 202, Columbus, Ohio 43212; Mark Foglietti, 3755 Orange Pl., Cleveland, Ohio 44122

[21] Appl. No.: 518,709

[22] Filed: May 4, 1990

[51] Int. Cl.$^5$ ............................................. A61F 2/12
[52] U.S. Cl. .................................................. 623/8
[58] Field of Search ..................................... 623/7, 8

[56] References Cited

U.S. PATENT DOCUMENTS

| | | | |
|---|---|---|---|
| 4,298,998 | 11/1981 | Naficy | 623/8 |
| 4,605,412 | 8/1986 | LaForest et al. | 623/8 |
| 4,648,880 | 3/1987 | Brauman | 623/8 |
| 4,650,487 | 3/1987 | Chaglassian | 623/8 |
| 4,773,909 | 9/1988 | Chaglassian | 623/8 |
| 4,790,848 | 12/1988 | Cronin | 623/8 |
| 4,820,303 | 4/1989 | Braumann | 623/8 |

FOREIGN PATENT DOCUMENTS 2199266  4/1974  France .................................. 623/8

*Primary Examiner*—Ronald Frinks
*Attorney, Agent, or Firm*—Longacre & White

[57] ABSTRACT

An improved breast prosthesis for insertion under the sub-cutaneous tissue or muscle of the chest wall formed as a plurality of compartments each containing silicone gel or the like. The surface area to volume ratio of the apical compartment is smaller than the basilar one so that the appearance of projection is produced and pressure on the apex results in basilar deformation, reducing the perception of apical firmness. Preferably the skin is of PTFE possibly reducing capsular contractive and the perception of excessive firmness.

8 Claims, 1 Drawing Sheet

MULTIPLE COMPARTMENT BREAST PROSTHESIS

BACKGROUND AND SUMMARY OF THE INVENTION

The invention relates to augmentation mammoplasty and reconstructive breast surgery and to an improved breast prostheses.

Conventional breast prostheses generally are constructed as a single unit containing gelatinous material such as silicone gel surrounded by a single envelope typically made of silicone. These prostheses are placed under the subcutaneous tissue of the breast or under the pectoralis muscle. The effect of the prosthesis is to enlarge the base of the breast. However, in many cases, and in particular after breast resection, enough subcutaneous tissue may not be present to provide adequate projection of the breast. The insertion of a larger prosthesis simply results in a pancaking effect since the prosthesis is soft to provide the normal feel of breast tissue and therefore tends to flatten. Increasing the viscosity of the gel within the breast can result in less flattening of the prosthesis. However, this also results in an abnormal sense of firmness of the breast. To compensate, a technique of stacking one prosthesis on top of another during surgical implantation of the breast has been proposed. However, such a technique can result in a flattening of both prostheses and is technically more difficult than the insertion of a single prosthesis.

A second problem relates to the formation of capsular contractures associated with tissue reaction to the implanted prosthesis. This problem is well known in the art and causes an abnormal sense of firmness of the enhanced breasts in a substantial percentage of patients.

In general, the improved breast prosthesis of the present invention is formed as a conical or pyramidal implant having a base which has a larger surface area than the apex which is preferably rounded. In the preferred embodiment the prosthesis includes a plurality of compartments which are surrounded by a single envelope. The base compartment has a larger surface area to volume ratio and therefore is more easily deformable than the more apical compartments. In other words, the walls of the basilar compartment are stretched less than the walls of the apical compartment and therefore the internal pressure is less as well.

In the preferred embodiment three compartments are provided, each with a progressively decreasing exterior surface area to volume ratio from the base to the apex. The compartments may be attached one to another as by adhesive and covered by a single envelope or they may be preferably integral, one with another, comprising individual compartments of a single pyramidal structure.

Each compartment is preferably filled with suitable permanent material such as conventional silicone. The surrounding envelope is preferably porous poytetrafluoroethylene, (PTFE) which can be obtained under the trade name GORTEX. The assembled prosthesis, when placed upon it's base, will assume a substantially conical shape having a rounded apex. The apical compartment will have a slighter firmer feel to palpation than the basilar compartment.

In operation the prosthesis is placed under the breast tissue or pectoralis muscle with the apex facing outwardly. The feel of the prosthetically enhanced breast will be substantially natural in that, while the apex of the breast is firmer than the base, pressure upon the apex results in basilar deformation thereby reducing the perception of apical firmness. However, the firmness of the apical portion produces the appearance of projection which is considered more aesthetically appealing to the patient. The porous polytetrafluoroethylene envelope provides a novel interface between the breast implant and the patient's surrounding tissue. This may potentialy reduce capsular contracture and therefore reduce the perception of excessive firmness which may develop with conventional implants.

DESCRIPTION OF THE PREFERRED EMBODIMENT

Figure 1:
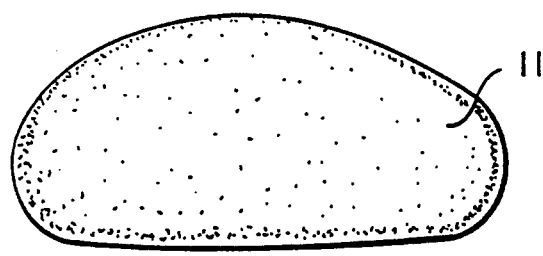
FIG. 1 is a side view of a conventional breast implant.
Figure 2:
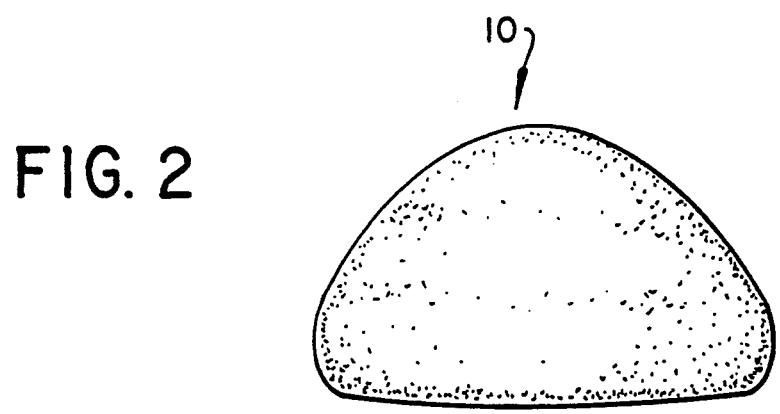
FIG. 2 is the side view of the preferred embodiment of the present invention.

The invention comprises, in general, an improved breast prosthesis 10 with a roughly conical or pyramidal shape having a rounded apex 12. More particularly, the prosthesis 10 resembles and responds to pressure like a natural breast. The tendency to flatten like a pancake which is inherent in a conventional prosthesis 11 as shown in FIG. 1 is avoided.

Figure 3:
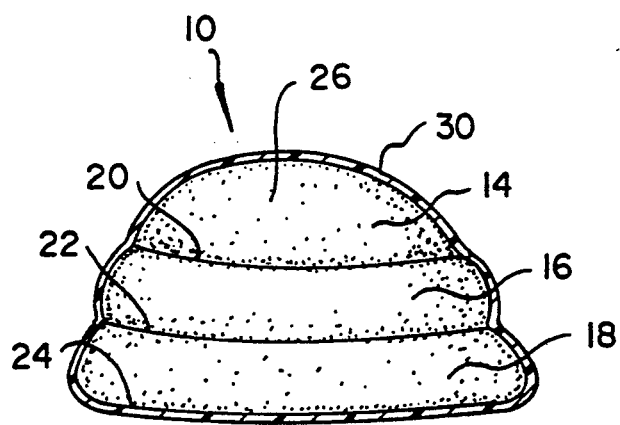
FIG. 3 is a sectional view through the apex of the preferred embodiment showing the three separate compartments.

FIG. 3 demonstrates the preferred embodiment in which this object is achieved by providing three separate compartments or chambers 14, 16, and 18 having respective interior walls 20, 22, and 24 which are integral one with another. Each compartment is filled with conventional silicone or other gel 26. The walls 20, 22, and 24 of the compartments 14, 16, and 18 are formed of silicone or other suitable material, as is known in the art. The compartments are isolated one from the other so that the contents thereof cannot readily migrate from compartment to compartment.

The basilar chamber 18 has a larger internal wall surface area to internal volume ratio than the middle chamber 16 and the middle chamber 16 has a larger internal wall surface area to internal volume ratio than the apical chamber 14. Thus, a greater sense of firmness in the apical chamber 14 is provided than in the basilar chamber 18 since the pressure at rest within the basilar chamber is less than in the apical chamber. In addition, this provides for apical projection when the prosthesis 10 is placed on the basilar compartment 18.

An outer surrounding envelope 30, preferably of porous polytetrafluoroethylene (PTFE), is provided to reduce tissue reaction to the prosthesis 10 and therefore reduce capsular contracture due to reaction of the patient's body tissue to the prosthesis.

Other approaches can be taken to providing that the multi-compartment prosthesis responds to pressure like a natural breast. The pressure in the respective compartments of the gel can be made deliberately different resulting in greater stretching in the apical compartment and a greater firmness. The firmness of the gel can likewise be deliberately made greater in the apical compartment by using gel having a greater viscosity.

Many other changes and modifications in the above described embodiments of the invention can of course be made without departing from the scope thereof. For example while three compartments are preferable more can be provided if desired and the invention provides good results with only a basilar and special compartment. Accordingly, that scope is intended to be limited only by the scope of the appended claims.

We claim:

1. An improved breast prosthesis for insertion under the subcutaneous tissue or muscle of the chest wall, the prosthesis comprising a deformable body defining a relatively conical shape with a base and apex, the apex having a relatively smaller topographical surface area than said base, the apex projecting away from said base when said base is placed in a dependent position relative to said apex, said body being divided into a middle compartment, a basilar compartment and an apical compartment, said middle compartment being intermediate said apical and said basilar compartment, said compartments being each formed with a wall having an interior surface area and defining an internal volume with said apical compartment having a smaller interior wall surface area to internal volume ratio than said basilar compartment, and wherein said middle compartment has a smaller internal surface area to volume ratio than said basilar compartment and a larger internal surface area to volume ratio than said apical compartment.

2. A prosthesis as in claim 1 wherein said apex is rounded.

3. The breast prosthesis of claim 1 wherein said walls of said compartments are integral one with another.

4. The breast prosthesis of claim 1 wherein said basilar compartment has a larger volume than said apical compartment.

5. The breast prosthesis of claim 1 wherein said body further comprises an outer housing means, said housing means comprising porous polytetrafluoroethylene.

6. An improved breast prosthesis for insertion under the subcutaneous tissue or muscle of the chest wall, the prosthesis comprising:

a deformable envelope defining apical, middle and basilar internal compartment isolated one from the other so that the contents thereof cannot readily migrate from compartment to compartment and stacked one on the other; and permanent deformable material in each of said compartments so said compartments form a relative conical shape from a base to an apex, the apical compartment having a lower surface area to volume ratio than the basilar compartment so as to have a greater resistance to deformation than the basilar compartment so that the appearance of projection is produced and pressure on the apex results in basilar deformation thereby reducing the perception of apical firmness, the three internal compartments defining an apical, a middle and a basilar compartment being stacked one a top the other and wherein the surface area to volume internal volume ratio of said apical compartment is less than the ratio of the middle compartment, and the ratio of said middle compartment is less than the ratio of said basilar compartment.

7. A prosthesis as in claim 6 wherein said envelope is formed of PTFE.

8. A prosthesis as in claim 6 wherein said deformable material is a silicone gel.

* * * * *